United States Patent [19]

Wall

[11] 4,079,085

[45] Mar. 14, 1978

[54] PROCESS FOR PREPARING ETHYLENE GLYCOL AND ETHYLENE GLYCOL ETHER

[75] Inventor: Robert G. Wall, Pinole, Calif.

[73] Assignee: Chevron Research Company, San Francisco, Calif.

[21] Appl. No.: 734,489

[22] Filed: Oct. 21, 1976

[51] Int. Cl.² ............................................. C07C 41/00
[52] U.S. Cl. ............................ 260/615 R; 260/635 R
[58] Field of Search ............ 260/615 R, 635 R, 635 A

[56] References Cited

U.S. PATENT DOCUMENTS 2,451,333  10/1948  Gresham et al. ................ 260/635 R Primary Examiner—Howard T. Mars
Attorney, Agent, or Firm—D. A. Newell; John Stoner, Jr.; W. Keith Turner

[57] ABSTRACT

Ethylene glycol and ethylene glycol ethers are prepared by hydroformylation of formaldehyde with carbon monoxide and hydrogen in the presence of a catalyst comprising a cobalt carbonyl, and rhodium.

6 Claims, No Drawings

PROCESS FOR PREPARING ETHYLENE GLYCOL AND ETHYLENE GLYCOL ETHER

BACKGROUND OF THE INVENTION

This invention concerns hydroformylation of formaldehyde to prepare ethylene glycol and ethylene glycol ethers. In particular, this invention concerns a single-step hydroformylation of formaldehyde using a catalyst comprising a cobalt carbonyl and rhodium.

U.S. Pat. No. 2,451,333 granted Oct. 12, 1948 illustrates the conventional two-step hydroformylation and reduction of formaldehyde. According to the disclosure, hydroformylation of formaldehyde using a cobalt catalyst yields a mixture of acetals and acetaldehyde, which can be reduced to ethylene glycol and ethylene glycol ethers. When the reaction is carried out in an alcohol solvent, the major product is the glycol ether.

It remains desirable to provide a single-step process for preparing ethylene glycol and its ethers which can be carried out under moderate reaction conditions.

SUMMARY OF THE INVENTION

This invention provides a single-step process for preparing a mixture of ethylene glycol and glycol ethers. The process comprises contacting formaldehyde with carbon monoxide and hydrogen in the presence of a catalyst comprising a cobalt carbonyl and rhodium. The process is carried out at a temperature of from about 100° C to about 200° C and a pressure of from about 1000 psig to about 10,000 psig.

DETAILED DESCRIPTION

The process of this invention employs a cobalt carbonyl and rhodium to catalyze the preparation of ethylene glycol and ethylene glycol ethers from formaldehyde, carbon monoxide and hydrogen.

The term "cobalt carbonyl" is used in the conventional sense to include cobalt complexes with carbon monoxide. Suitable carbonyls may be either pure carbonyls wherein carbon monoxide forms a stable complex with the lowest oxidation state of cobalt, or cobalt carbonyls bound to an additional moiety such as a halide or hydride. Thus, carbon monoxide acts as either a monodentate ligand or a divalent bridging group. Suitable cobalt carbonyls can be monomeric, dimeric, or polymeric.

In general, cobalt carbonyls suitable for use as catalysts in the process of this invention are of the formula $$Co(CO)_n (X)_m$$

wherein $X$ is an anionic ligand bound to the cobalt ion, $n$ is 1 to 6, $m$ is 0 to 6, and $n+m$ is 3 to 6. The coordination number of the cobalt ion is represented by $n+m$, and the valence or oxidation state of the cobalt moiety is represented by $m$. This formula depicts only the empirical composition which may also exist in dimeric or polymeric form. Cobalt octacarbonyl is an especially preferred catalyst. The cobalt carbonyl compound can be formed in advance and introduced into the reaction zone, or, it may be formed in situ from a suitable precursor. For example, $CoCO_3$ has been found to be a precursor for cobalt carbonyls under the conditions of this process.

Rhodium is the second component of the catalyst. It can be incorporated in the catalyst as either elemental rhodium metal or a rhodium containing compound. Rhodium exists in five oxidation states ranging from the zero state to the tetrapositive state. Of the positive oxidation states exhibited, the tripositive state is the most stable. Accordingly, the tripositive rhodium compounds are preferred. The oxides, halides and sulfates are examples of suitable rhodium tripositive compounds. The halo and cyano compounds and the amine complexes are also acceptable.

Rhodium (III) oxide, $Rh_2O_3$ is an especially preferred rhodium compound. It is formed when powdered rhodium metal is heated in air above 600° C. Slow addition of alkali to solutions of tripositive rhodium results in the precipitation of the yellow hydrate $Rh_2O_3.5H_2O$, which is also preferred.

Anionic complexes of tripositive rhodium with all the halogens are acceptable. Those with fluorine, chlorine, and bromine being particularly preferred. The anhydrous rhodium trihalides are representative halo compounds. They are obtained by appropriate direct union of the elements. The iodide can also be prepared by precipitation from aqueous solution. The trifluoride is a dark red substance, practically inert to water, acids and bases. The trichloride, as prepared by direct union, is also red and is insoluble in water and acids. Evaporation of a solution of rhodium (III) oxide hydrate in hydrochloric acid yields $RhCl_3.4H_2O$. Removal of the water of crystallization at 180° C in a hydrogen chloride atmosphere gives an anhydrous trichloride which is water-soluble; heating of this latter material to higher temperatures converts it to the water-insoluble form.

The rhodium sulfate hydrates are preferred sulfates. The best known are $Rh_2(SO_4)_3.14H_2O$ and $Rh_2(SO_4)_3.6H_2O$. The former is a yellow material obtained by dissolving the oxide hydrate in cold dilute sulfuric acid and crystallizing by evaporation in vacuo at 0°; the red hexahydrate is prepared by evaporating an aqueous solution of the 14-hydrate to dryness at 100° C. From aqueous solutions of the 14-hydrate all the sulfate is immediately precipitated by addition of barium ion.

Cationic amine complexes of rhodium (III) are also suitable sources of rhodium. Representative compound types include, among others, $[Rh(NH_3)_6]X_3$, $[Rh(NH_3)_3]X_3$, $[Rh(NH_3)_5(H_2O)]X_3$, and $[Rh(NH_3)_5R]X_2$ (R=monovalent acid radical or OH— group) wherein X is a suitable anion, for example halide.

Suitable anionic rhodium complexes include, for example, $MI_3[Rh(CN)_6]$, $MI_3[Rh(NO_2)_6]$, $MI_3[Rh(SO_4)_3]$, $MI_3[Rh(SO_3)_3]$, and $MI_3[Rh(C_2O_4)_3]$ wherein M is a suitable cation, for example alkali metal. Solutions of the cyano complexes are particularly stable.

Effective catalyst concentrations will vary depending upon the reaction conditions employed. In general, the process can be carried out in the presence of a catalytically effective amount of a catalyst comprising a cobalt carbonyl and rhodium. The relative weight proportion of cobalt carbonyl to rhodium is not critical, but will typically range from about 1:10 to about 10:1. The reaction starts readily at catalyst concentrations of only 0.3 weight %, although even small quantities are effective. The maximum concentration may go as high as 10 weight %. However, in practice, economic considerations will limit the concentration as no appreciable advantages are gained by concentrations above about 5 weight %. Typical catalyst concentrations will range from about 0.1 to about 5 weight %, preferably from about 0.3 to about 3 weight %.

The temperature of reaction is relatively mild. Temperatures as low as 100° C are acceptable. In general, the process is carried out at temperatures from about 130° C to about 200° C. Higher temperatures do not significantly improve the reaction rate, while lower temperatures appreciably decrease the reaction rate.

The reaction is carried out under moderate pressure. In general, the overall pressure will not greatly exceed the partial pressure of carbon monoxide and hydrogen which are by far the more volatile of the reactants. Pressures from about 1000 psig to about 10,000 psig are suitable. At lower pressures, the rate of reaction is relatively slow, while at higher pressures, no appreciable advantage is obtained. Preferred pressures range from about 1000 psig to about 5000 psig. At higher temperatures the cobalt carbonyl may lose stability consequently reducing the yield of glycol and glycol ethers. In order to direct the reaction toward increasing yields, higher partial pressures of carbon monoxide and hydrogen are employed.

The residence time required for the reaction to reach completion may range from a few minutes to several hours, depending upon the concentration of reactant and reaction conditions. In general, a residence time of from about 1 hr to about 5 hrs will be necessary to reach completion under preferred reaction conditions. In practice it may be advantageous to continuously recover product thereby driving the reaction toward production of glycol and ether. Completion is defined as the point at which the amount of formaldehyde converted to product as a function of time does not appreciably increase.

The relative proportions of formaldehyde, carbon monoxide and hydrogen may vary over a wide range. In general, a molar ratio of $CH_2O:CO:H_2$ from about 1:20:1 to about 1:1:20, preferably from about 1:20:1 to about 1:1:10, is suitable. Reaction mixtures capable of forming carbon monoxide and hydrogen under the reaction condition may be used instead of the gas mixtures.

The process may be carried out batchwise or continuously, in a single reaction zone or in a number of reaction zones. In a preferred embodiment Synthesis Gas, comprising carbon monoxide and hydrogen, is passed counter-current to formaldehyde and the catalyst mixture in cascade fashion. In the preferred continuous process, for instance when operating at lower conversions, it is desirable to recycle any unreacted Synthesis Gas with fresh gas. Recovery of the products may be accomplished by any of the usual methods, such as distillation, fractionation, extraction, etc. A fraction containing the catalyst, generally in a secondary product or diluent, may be recycled. This fraction may, however, be entirely or partially reprocessed or the catalyst may be regenerated. Fresh catalyst may be added to the recycle stream.

The process of this invention may be carried out in the presence of a solvent. Examples of organic liquids suitable for use as solvents include ethers such as tetrahydrofuran, diethyl ether and the like; and alkanols such as ethanol, methanol, 2- ethylhexanol and the like.

The following Examples further illustrate practice of the process of this invention. The Examples are representative and are not intended to limit the invention. Those familiar with the art will readily perceive modifications of the process in view of the Examples.

EXAMPLES

EXAMPLE I

A 300 cc Autoclave Engineers Magnedrive Autoclave was charged with 16 g of paraformaldehyde, 50 g of methanol, 2 g of cobalt carbonyl $[CO_2(CO)_8]$ and 0.1 g of N-(carboxymethyl)-$N^1$-(2-hydroxyethyl)-N,$N^1$-ethylenediglycine. The reaction was run at 180° C for 2.5 hours using 67% $H_2$/33% CO at 2800 psig. Vapor chromatographic analysis with an internal standard showed the product to contain 6.3 g total of 2-methoxyethanol and ethylene glycol. This amounts to a 16% yield based on the charged formaldehyde.

EXAMPLE II

The autoclave used in Example I was charged with 16 g of paraformaldehyde, 50 g of ethanol and 0.2 g of $Rh_2O_3.5H_2O$. The reaction was run with 67% $H_2$/33% CO at 3300 psig and 150° C for 2 hours. The product contained 2.8 g (8.8% yield) of ethylene glycol.

EXAMPLE III

The autoclave used in Example I was charged with 16 g of paraformaldehyde, 50 g of ethanol, 0.2 g of cobalt carbonyl and 0.5 g of $Rh_2O_3.5H_2O$. The reaction was run with 67% $H_2$/33% CO at 3100 psig and 150° C for 5 hours. The product contained 4.1 g of ethylene glycol and 9.7 g of 2-ethoxyethanol for a combined yield of 35% on the charged formaldehyde.

EXAMPLE IV

The autoclave used in Example I was charged with 16 g of paraformaldehyde, 50 g of ethanol, 1 g of cobalt carbonyl and 0.2 g of $Rh_2O_3.5H_2O$. The reaction was run with 67% $H_2$/33% CO at 2700 psig and 130° C for 3 hours. The product contained 1.8 g of ethylene glycol (5.7% yield) and 4.7 g of 2-ethoxyethanol (10.2% yield).

EXAMPLE V

The autoclave used in Example I was charged with 50 g of methylal, 0.2 g of cobalt carbonyl and 0.2 g of $Rh_2O_3.5H_2O$. The reaction was run with 67% $H_2$/33% CO at 3000 psig and 150° C for 3 hours. The product contained 14 g total of 2-methoxyethanol and ethylene glycol. This corresponds to a 30% yield based on charged methylal.

EXAMPLE VI

The autoclave used in Example I was charged with 50 g of methylal, 0.2 g of cobalt carbonyl and 0.2 g of $Rh_2O_3.5H_2O$. The reaction was run with 67% $H_2$/33% CO at 2900 psig and 180° C for 4.5 hours. The product contained 12.2 g total of 2-methoxyethanol and ethylene glycol for a yield of 24%.

Examples I through VI show that the cobalt carbonyl-$Rh_2O_3.5H_2O$ catalyst combination gives better yields of ethylene glycol and ethylene glycol ethers than $Rh_2O_3.5H_2O$ or cobalt carbonyl alone using a 67% $H_2$/33% CO synthesis gas.

EXAMPLE VII

The autoclave used in Example I was charged with 16 g of paraformaldehyde, 50 g of ethanol and 1 g of cobalt carbonyl. The reaction was run with 50% $H_2$/50% CO at 3000 psig and 180° C for 2 hours. The product contained 1 g of ethylene glycol and 5 g of 2-ethoxyethanol for a combined 14% yield.

EXAMPLE VIII

The autoclave used in Example I was charged with 16 g of paraformaldehyde, 50 g of ethanol and 0.2 g of $Rh_2O_3 \cdot 5H_2O$. The reaction was run with 50% $H_2$/50% CO at 3000–3500 psig and 130° C for 5 hours and another 6.5 hours at 3000–3300 psig and 150° C. The product contained 2.9 g (9% yield) of ethylene glycol.

EXAMPLE IX

The autoclave used in Example I was charged with 16 g of paraformaldehyde, 50 g of ethanol, 0.5 g of cobalt carbonyl and 0.2 g of $Rh_2O_3 \cdot 5H_2O$. The reaction was run with 50% $H_2$/50% CO at 3000 psig and 150° C for 3 hours. The product contained 1.6 g of ethylene glycol and 4.7 g of 2-ethoxyethanol for a combined yield of 15.1%.

What is claimed is:

1. A process for preparing ethylene glycol and glycol ethers which comprises contacting formaldehyde, carbon monoxide, and hydrogen in the presence of a catalytic amount of a catalyst comprising a cobalt carbonyl and rhodium metal or a rhodium-containing compound, the weight ratio of the cobalt carbonyl component to the rhodium component ranging from about 1:10 to about 10:1, at a temperature of from about 100° C to about 200° C and a pressure of from about 1000 psig to about 10,000 psig.

2. A process according to claim 1 wherein said cobalt carbonyl is cobalt octacarbonyl.

3. A process according to claim 1 wherein said rhodium is a tripositive rhodium oxide.

4. A process according to claim 1 wherein the catalyst concentration is from about 0.1% to about 5%.

5. A process according to claim 1 wherein the molar ratio of formaldehyde to carbon monoxide to hydrogen is from about 1:20:1 to about 1:1:20.

6. A process according to claim 1 wherein the temperature is from about 120° C to about 180° C, the pressure is from about 2000 psig to about 5000 psig, and the catalyst comprises cobalt octacarbonyl and tripositive rhodium oxide.

* * * * *